United States Patent [19]
Herrmann et al.

[11] Patent Number: 6,119,034
[45] Date of Patent: Sep. 12, 2000

[54] MEDICAL SYSTEM HAVING AN X-RAY MACHINE AND A THERAPY UNIT WITH A SOURCE OF FOCUSED ACOUSTIC WAVES, AND A METHOD FOR COUPLING THE THERAPY UNIT TO THE X-RAY MACHINE

[75] Inventors: Klaus Herrmann, Nuremberg; Guenther Winkelmann, Herzogenaurach, both of Germany

[73] Assignee: Siemens Aktiengesellschaft, Munich, Germany

[21] Appl. No.: 09/178,152

[22] Filed: Oct. 23, 1998

[30] Foreign Application Priority Data

Oct. 23, 1997 [DE] Germany ............... 197 46 956

[51] Int. Cl.[7] ........................................... A61B 5/00
[52] U.S. Cl. ................... 600/427; 601/2; 601/4; 378/197
[58] Field of Search ............... 601/2–4; 600/427, 600/439; 378/197, 205

[56] References Cited

U.S. PATENT DOCUMENTS

| | | |
|---|---|---|
| 4,984,575 | 1/1991 | Uchiyama et al. . |
| 5,285,772 | 2/1994 | Rattner . |
| 5,327,890 | 7/1994 | Matura et al. . |
| 5,395,299 | 3/1995 | Herrmann et al. . |
| 5,488,951 | 2/1996 | Bauer et al. . |
| 5,583,901 | 12/1996 | Reitter et al. . |
| 5,836,898 | 11/1998 | Schwieker ............... 601/4 |

FOREIGN PATENT DOCUMENTS 44 43 495  6/1996  Germany .

*Primary Examiner*—Ruth S. Smith
*Attorney, Agent, or Firm*—Hill & Simpson

[57] ABSTRACT

A medical system has an X-ray apparatus with an X-ray system having an X-ray source and an X-ray receiver, and a therapy unit with a source of focused acoustic waves, the therapy unit being detachably coupleable to the X-ray apparatus. A method for coupling the therapy unit to the X-ray apparatus is also disclosed. The coupling is performed so that after the therapy unit has been coupled to the X-ray apparatus the focus of the acoustic wave source is situated at least approximately in the beam path of the central beam of an X-ray bundle proceeding from the X-ray source to the X-ray receiver, and the X-ray system can be adjusted relative to the source.

25 Claims, 9 Drawing Sheets

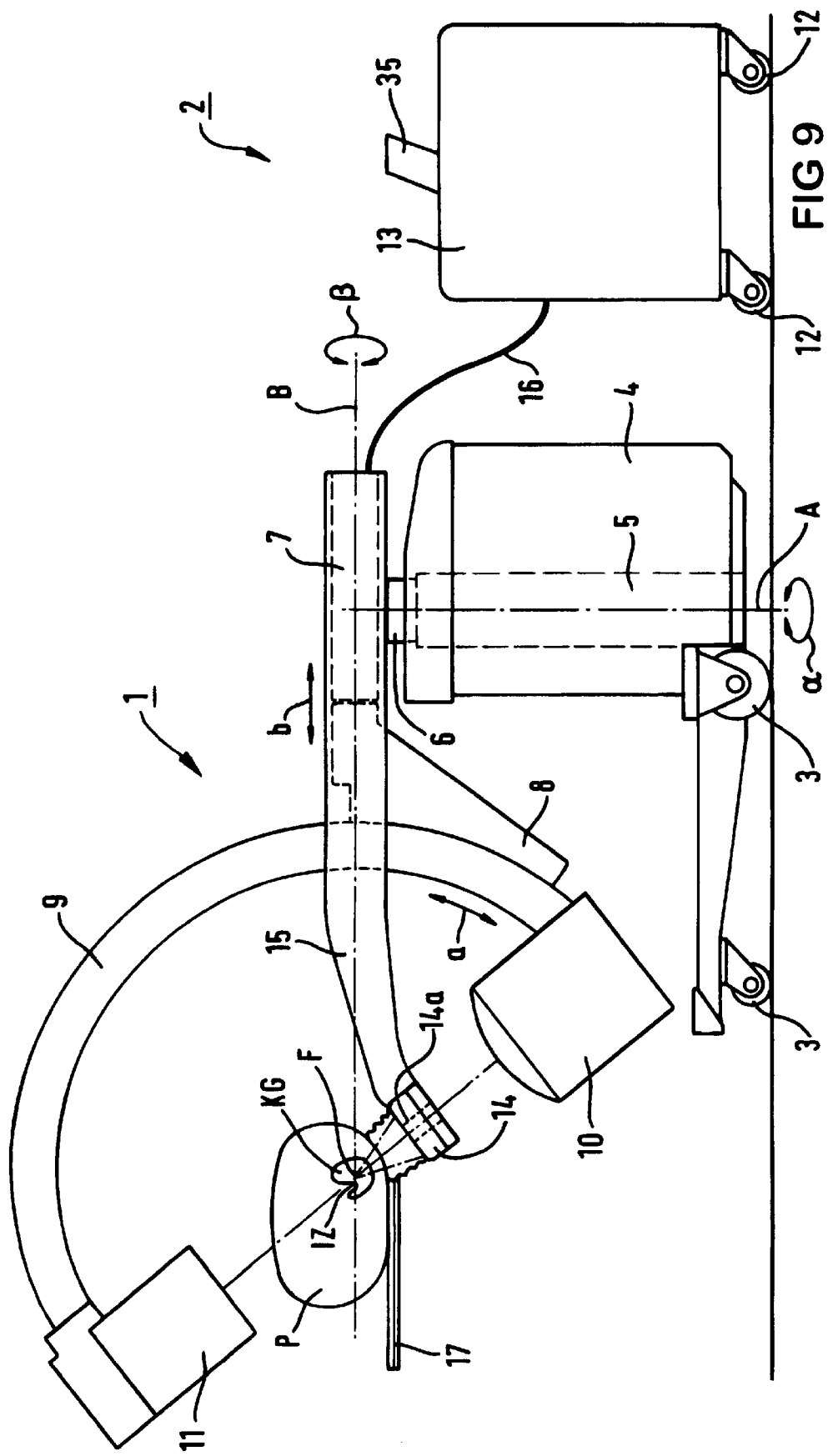

MEDICAL SYSTEM HAVING AN X-RAY MACHINE AND A THERAPY UNIT WITH A SOURCE OF FOCUSED ACOUSTIC WAVES, AND A METHOD FOR COUPLING THE THERAPY UNIT TO THE X-RAY MACHINE

BACKGROUND OF THE INVENTION

1. Field of the Invention

The present invention relates to a medical system of the type having an X-ray machine with an X-ray system having an X-ray source and an X-ray receiver which can be adjusted relative to an object, and having a therapy unit, with a source for generating acoustic waves converging at a focus, which can be coupled to the X-ray machine. The invention also relates to a method for coupling the therapy unit to the X-ray machine.

2. Description of the Prior Art

Medical systems of this type are used, for example, in pain therapy, bone restoration, for disintegrating concrements in the body of a patient or for treating body tissue, for example tumorous tissue. Generally, the concrement or the body tissue is located with the aid of the X-ray machine and moved to the focus of the source of acoustic waves, after which focused acoustic waves are applied to the concrement or tissue.

A medical system of this general type is known, for example, from European Patent 0 606 548, which corresponds to German PS 43 00 740, which has a mobile X-ray machine, with an X-ray system arranged on a C arm, and a therapy unit with an electro-acoustical transducer for generating focused sound waves. The therapy unit can be detachably connected to the C-arm of the X-ray machine via a coupling device, it being possible for the C-arm to be pivoted around the focus of the transducer after being coupled to the therapy unit. The C-arm follows the pivoting movement of the transducer in this case.

U.S. Pat. No. 4,984,575 describes a medical system which has an X-ray machine, which is provided with an X-ray system having a vertically adjustable X-ray source and a fixed X-ray receiver, and a therapy unit with a source for generating focused acoustic waves. The source is detachably arranged on the X-ray source by means of a holding arm such that the source executes the same movements as the X-ray source in the event of a vertical adjustment of the X-ray source.

It has proven to be a disadvantage of these known medical systems that it is necessary, before coupling, for the therapy unit and the X-ray machine to be aligned relative to one another in a complicated and lengthy process so that the focus of the source is situated at least approximately in the beam path of the central beam of an X-ray bundle emitted by the X-ray source and proceeding to the X-ray receiver. A further disadvantage is that the therapy unit can be coupled to the X-ray machine, and/or the source of focused acoustic waves can be coupled to the X-ray source, only in such a way that the possibilities of using the X-ray system for X-ray locating and X-ray monitoring are limited by the coupling of the X-ray source and the source of focused acoustic waves.

German OS 44 43 495 discloses a therapy unit having a lithotriptor with a carriage and, arranged thereon, a fixed-focus shock wave generator, and having an X-ray machine for X-ray locating with a carriage and, arranged thereon, a C-arm carrying an X-ray tube assembly and an X-ray image converter. The carriage of the therapy unit can be coupled to the carriage of the X-ray machine in such a way that, after coupling, the focus of the shock wave generator is situated on the central beam, at least at the locating positions, this central beam proceeding from the X-ray tube assembly to the X-ray image converter.

A disadvantage of this known lithotriptor is that additional alignment processes are required so that, after coupling, the focus of the shock wave generator is situated not only on the central beam of the X-ray bundle proceeding from the X-ray tube assembly to the X-ray image converter, but also, as is frequently desired, on the angulation axis of the X-ray machine. Moreover, the coupling of the carriages is inconvenient and requires a certain expenditure of force, since the carriages must be pushed precisely into engagement with one another, one carriage being raised by the other in order to be able to move the carriages jointly.

Another apparatus for treating organisms with acoustic waves is known from German OS 41 30 761. Arranged on a C-arm of the apparatus are an X-ray system, including an X-ray source and an X-ray receiver, and a source of acoustic waves which can be adjusted on the inner circumference of the C-arm. The X-ray system and the source, however, are not components of units which are designed separately from one another and can be detachably coupled to one another.

SUMMARY OF THE INVENTION

It is an object of the present invention to provide a medical system of the initially designed general type wherein the coupling of the therapy unit to the X-ray machine is simplified, and the possibilities for X-ray locating and X-ray monitoring by means of the X-ray system are extended. It is also an object of the invention to provide a simple and quick method for coupling the therapy unit to the X-ray machine.

According to the invention, the object relating to the medical system is achieved in a medical system having an X-ray machine with an X-ray system having an X-ray source and an X-ray receiver, can be adjusted relative to an object, and arranged on a machine part and/or connected to a machine part which can be vertically adjusted at least indirectly and/or can be pivoted around a horizontally extending axis, which can be adjusted vertically together with the machine part, of the X-ray machine. The inventive medical system also has a therapy unit with a source, arranged on a support arm for generating acoustic waves which converge at a focus, which support arm can be detachably coupled, at least indirectly, to the machine part such that after the support arm has been coupled to the machine part, the focus of the source is situated at least approximately on the horizontally extending axis of the X-ray machine and in the beam path of the central beam of an X-ray bundle proceeding from the X-ray source to the X-ray receiver, and the X-ray system can be adjusted relative to the source. In the inventive system, the support arm of the therapy unit is coupled, at least indirectly, to the machine part of the X-ray machine in a fashion so that, without complicated aligning processes as are described, for example, in European Patent 0 606 548 or as are required in the apparatus of German OS 44 43 495, the focus of the source is situated at least approximately on the horizontally extending axis of the X-ray machine and in the beam path of the central beam of the X-ray bundle proceeding from the X-ray source to the X-ray receiver. Since the X-ray system of the X-ray machine can be adjusted relative to the source of acoustic waves even after the support arm has been coupled to the X-ray machine, the possibilities for X-ray locating concrements or body tissue in a patient are extended, in addition. As a result, it is possible, for example, without simultaneously displacing the source to prepare radiographs from different directions of concrements or of a body tissue in a patient for the purpose of monitoring the progress of a treatment with focused acoustic waves. Coupling the support arm carrying the source to the machine part of the X-ray machine can be accomplished in this case in a simple way and without a special expenditure of force. "Indirectly coupling" the support arm of the source to the machine part means that the support arm can be coupled to the machine part via interviewing coupling or support elements or mechanisms.

In one embodiment of the invention, the source having an acoustic axis is provided with a central X-ray transparent region. It is preferable, after the support arm has been coupled to the X-ray machine, for the central beam of the X-ray bundle proceeding from the X-ray source to substantially coincide with the acoustic axis of the source. Such a source thus can also be arranged relative to the X-ray machine such that the central beam of the X-ray bundle emitted by the X-ray source extends through the X-ray transparent region of the source of acoustic waves.

In another embodiment of the invention the X-ray machine has a support device or carrier for the X-ray system which is mounted in a bearing assembly arranged on a holder. In variations of this embodiment, the carrier of the X-ray machine is constructed in the shape of a C-arm, and can be adjusted along its circumference in the bearing assembly, and has an isocenter, i.e. the beam path of the central beam of the X-ray bundle emitted by the X-ray source proceeds through the fulcrum of the C-arm. This is particularly advantageous when the C-arm can be coupled to the X-ray source such that the focus of the source is located at the isocenter of the C-arm. During adjustment of the C-arm, for example along its circumference (orbital movement), the central beam always extends through the isocenter of the C-arm, and therefore also through the focus of the source. Thus, the central beam does not go out of focus when the C-armis adjusted.

In another embodiment of the invention the bearing assembly arranged on the holder, and the carrier arranged on support bearing, can be pivoted around the horizontal axis, which proceeds through the holder. It is preferable to be able to displace the bearing assembly with reference to the holder along the horizontal axis. In this way, the X-ray machine offers many possibilities for setting the X-ray system relative to an object, for example relative to a patient to be treated, for the purpose of X-ray locating of concrements or body tissue in the patient.

In a further embodiment the therapy unit is provided with a drive device which can be coupled to a drive element, which extends through the holder, and is connected to the bearing assembly, and contains the horizontal axis, such that the bearing assembly can be pivoted around the horizontal axis together with the carrier by means of the drive device co-operating with the drive element. In this case, the drive device is, for example, provided with an electric motor so that after the support arm of the source has been coupled to the X-ray machine, and the drive device of the therapy unit has been coupled to the drive element, the pivoting movement of the bearing assembly and/or of the carrier about the horizontally extending axis of the X-ray machine can be performed by motor.

In another embodiment of the invention, the therapy unit has a holder on which the support arm carrying the source is arranged, the support arm being removeable from the holder. This is particularly advantageous when the therapy unit is of mobile design, because after the support arm has been coupled to the X-ray machine the therapy unit can be positioned in a fashion spatially separated from the X-ray machine. In this way, a person treating a patient with the medical system, for example, has more room at his or her disposal at the X-ray machine and at the source of focused acoustic waves, and the X-ray machine and the source of focused acoustic waves are also effectively accessible on all sides after the support arm of the source has been coupled to the X-ray machine. The source on the support arm is connected in this case via lines to a remote carriage of the therapy unit which is disposed spatially from the remainder of the therapy unit and contains the devices required to operate the acoustic wave source. The defined coupling of the support arm to the X-ray machine is preferably made so that the coupling point on the X-ray machine is situated as close as possible to the X-ray system, with the result that the support arm can be arranged on the X-ray machine with only a slight projection. This results, after the coupling, in the position of the focus of the source being situated relatively accurately in the beam path of the central beam of the X-ray bundle emitted by the X-ray source.

In another embodiment of the invention, the therapy unit has a holder on which there is arranged a bearing device in which the support arm of the source is displaceably mounted. The coupling of the therapy unit to the X-ray apparatus is performed in this case by coupling the bearing device to a component of the X-ray apparatus. Because of the displaceable mounting of the support arm in the bearing device, after the bearing device has been coupled to the component of the X-ray apparatus the support arm can placed in different positions with respect to the X-ray apparatus. The support arm preferably can adopt at least two defined positions in the bearing device. One position is adopted by the support arm preferably when the therapy unit is being transported, or when the therapy unit is being coupled to the X-ray machine, the source arranged on the support arm being located relatively close to the carriage of the therapy unit. The second defined position is the so-called therapy position of the support arm, into which the support arm and the source arranged thereon can be brought after the therapy unit has been coupled to the X-ray machine, the focus of the source being situated at least approximately on the horizontal axis and on the central beam of the X-ray system.

In variations of this embodiment the bearing device can be removed from the holder, and the holder can have a substantially horizontal axis around which the bearing device can be pivoted. The fact that the bearing device can be removed from the holder allows in the case of the medical system, more free room for staff around the X-ray machine, since the therapy unit can be positioned in a fashion remote from the X-ray machine. The pivotability of the bearing device is advantageous for transport operations of the therapy unit, since the support arm, which normally projects outwardly, can be brought into a vertical position by pivoting around the axis by approximately 90°, thus having little disturbing effect on the transport operation.

In a further embodiment of the invention the bearing device of the therapy unit has a holding device on which the drive device is arranged. In a variant of this embodiment, the drive device is arranged in this case so as to be longitudinally displaceably on the holding device and/or in a fashion capable of being pivoted about the holding device. The arrangement of the drive device on the holding device of the bearing device makes it possible, after the support arm has been coupled to the machine part of the X-ray machine, for the drive device to be coupled in a simple way to the drive element arranged in the holding part, in order to be able to effect the pivoting of the support device by motor.

In further variants of this embodiment the support arm and the bearing device have a coupling device which co-operates with the coupling device for the machine part of the X-ray machine for the purpose of coupling the therapy unit to the X-ray machine. The coupling device of the support arm or the bearing device, and the coupling device of the X-ray machine are provided in this case, in accordance with a further variant of the invention, with positioning aids which permit the therapy unit to be coupled simply, quickly and reliably to the X-ray machine.

In a further variant the coupling device of the X-ray machine has a coupling plate provided with the aforementioned positioning aids, the positioning aids of the coupling plate being formed by a positioning nose and an approximately vertically extending aperture and the positioning aids of the coupling device comprising a positioning groove and a positioning bolt. During coupling, the positioning bolt engages in the aperture, and the positioning nose engages in the positioning groove. By virtue of the fact that the positioning nose of the coupling plate of the X-ray machine cooperates with the corresponding positioning groove of the coupling device, and the positioning bolt of the coupling device co-operates with a corresponding aperture in the coupling plate, the therapy unit can be coupled to the X-ray machine in a simple, quick and reliable way.

In another embodiment of the invention, the coupling device of the therapy unit has a mechanism for locking the coupling device with the coupling device of the X-ray machine. This prevents the coupling of the therapy unit to the X-ray machine from being loosened inadvertently.

The support arm and the bearing device of the source arm of the acoustic wave source can be coupled to the holding part of the X-ray machine. In this case, the support arm provided with the source is constructed so that after the support arm or the bearing device has been coupled to the supporting part, the focus of the source is situated at least approximately in the beam path of the central beam of an X-ray bundle. The carrier in the shape of a C-arm can, furthermore, be adjusted in position relative to the source along its circumference (orbital movement), and the bearing assembly can be pivoted with the C-arm carrier around its axis, at least within certain limits which can be influenced by the geometry of the support arm (angulation).

The support arm of the source and the bearing device for the support arm carrying the source can be coupled to the bearing assembly. The support arm is designed in this case in such a way that after the support arm or the bearing device has been coupled to the bearing assembly, the focus of the source is situated at least approximately in the beam path of the central beam of an X-ray bundle, and the C-arm carrier can be adjusted relative to the source of focused acoustic waves along its circumference in the bearing assembly (orbital movement).

The support arm for the acoustic wave source and the bearing device for this support arm can be coupled to the C-arm carrier. In this case, coupling the support arm or the bearing device to the carrier is preferably performed via a pivot joint arranged on the carrier. The defined coupling of the support arm or the bearing device to the pivot joint is effected in this case by virtue of the fact that after the support arm or the bearing device has been coupled to the carrier, the focus of the acoustic wave source is situated at least approximately in the beam path of the central beam of an X-ray bundle, and the bearing assembly can be pivoted together with the carrier and its axis, at least within certain limits, relative to the source of focused acoustic waves (angulation). In this embodiment of the invention, the support arm remains in fixed contact with the therapy unit as a rule, as a result of which the support arm is stabilized.

The object relating to the method is achieved in a method for coupling the therapy unit to the X-ray machine, the X-ray machine being provided with a lifting column, which can be rotated around its central axis and which has brakes, and on which the aforementioned holder is arranged, and the therapy unit and/or the X-ray machine being of mobile design, the method having the following method steps:

a) Releasing the brakes to allow adjustment of the lifting column, b) Aligning the X-ray machine and the therapy unit relative to one another such that the positioning bolt of the coupling device of the therapy unit engages in the aperture in the coupling plate of the coupling device of the X-ray machine, causing the coupling device of the therapy unit to bear at least partially against the coupling plate, c) Vertically adjusting the lifting column of the X-ray machine in such a way that the positioning nose of the coupling plate comes to be situated in the positioning groove of the coupling device, d) Locking the mechanism of the coupling device of the therapy unit in order to couple the therapy unit to the X-ray machine, and e) Applying the brakes for the purpose of fixing the lifting column of the X-ray machine.

Coupling the therapy unit to the X-ray machine by using the method according to the invention advantageously permits a simple, quick and reliable coupling of the therapy unit to the X-ray machine.

DESCRIPTION OF THE DRAWINGS

FIG. 9 shows the medical system according to the invention from FIG. 1, wherein the C-arm has been rotated from the position shown in FIG. 1 to a position wherein the central ray from the x-ray source proceeds through the acoustic wave source.

DESCRIPTION OF THE PREFERRED EMBODIMENTS

Figure 1:
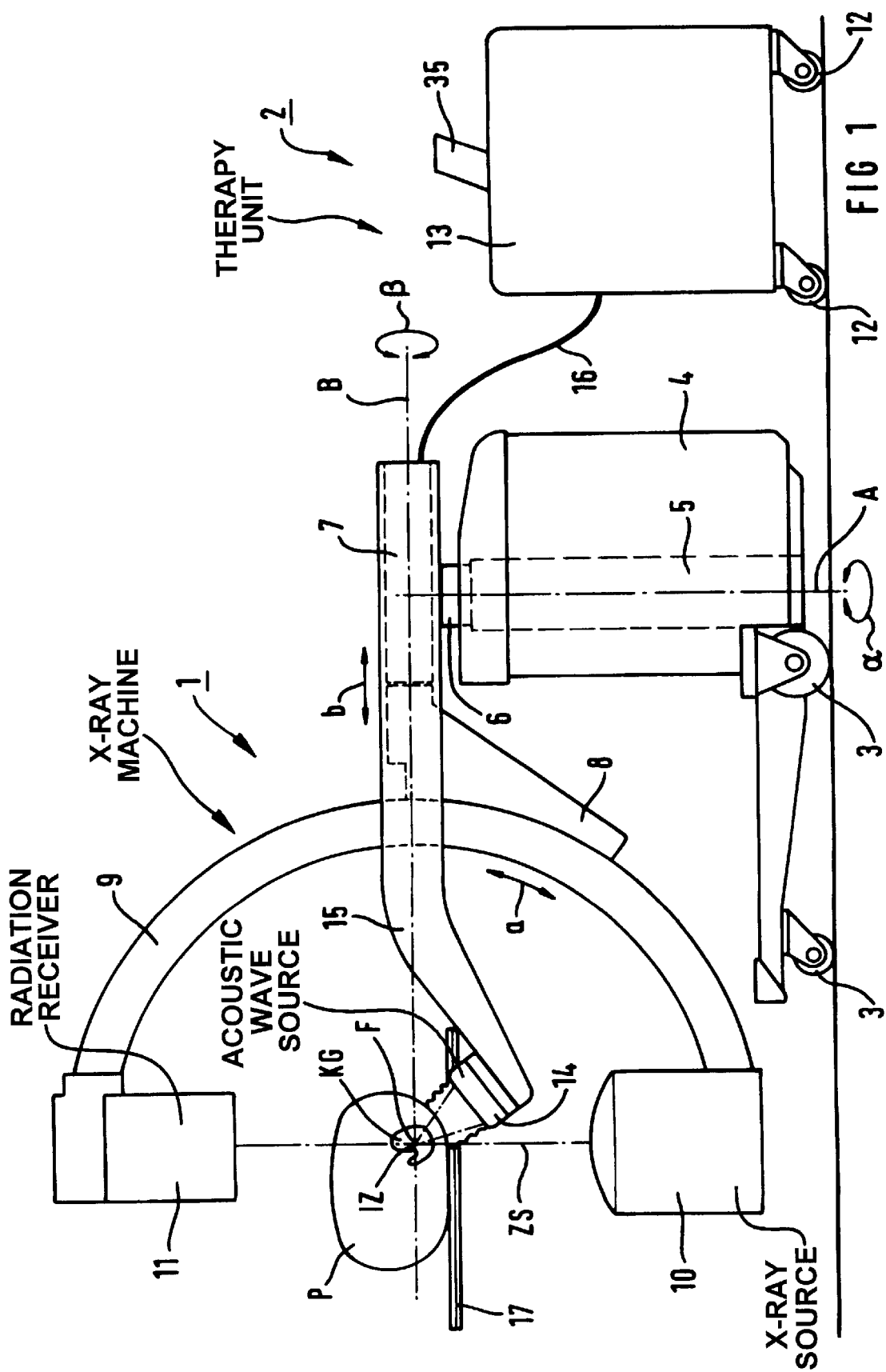
FIG. 1 shows a medical system according to the invention, in which the support arm of the source is coupled to the holder of an X-ray apparatus and is removed from the holder of the therapy unit.

FIG. 1 shows a medical system according to the invention having a C-arm X-ray apparatus 1 and a therapy unit 2.

The C-arm X-ray apparatus 1 has an apparatus cart or carriage 4, which can move on wheels 3, and is provided with a lifting device 5 (indicated only schematically in FIG. 1) with a lifting column 6 which has a longitudinal axis A around which the lifting column 6 can be rotated in the direction of the double arrow. Arranged on the lifting column 6 is a holder 7 on which, in turn, a bearing assembly 8 is arranged for bearing a C-arm 9 having an isocenter IZ. The C-arm 9 carries at its ends an X-ray source 10 and an X-ray receiver 11, which form an X-ray system and which are arranged opposite each other so that the central beam ZS of an X-ray bundle emitted by the X-ray source 10 strikes approximately centrally on the X-ray receiver 11. The C-arm 9 is mounted in the bearing assembly 8 in a known manner such that it can be displaced along its circumference in the direction of the double arrow a. The bearing assembly 8 is mounted in a known manner such that it can pivot around a common horizontal axis B of the holder 7 and the bearing assembly 8 (double arrow β) and can be displaced in the direction of the axis B (double arrow b). The C-arm 9, which is connected via the bearing 8 and the holding part 7 to the lifting column 6 of the lifting device 5, can be adjusted vertically relative to the carriage 4 by the lifting device 5.

The therapy unit 2 has a carriage 13 which can be moved on wheels 12, and a support arm 15 which is provided with an acoustic wave source 14, of a known type for generating acoustic waves converging at a focus F, as is described, for example, in German OS 41 35 177. The carriage 13 also has a holder 35 for the support arm 15, from which the support arm 15 can be removed. In FIG. 1, the support arm 15 has been removed from the holder 35 and coupled to the holder 7 of the C-arm X-ray apparatus 1. The source 14 is connected via the support arm 15 and supply lines 16 to the unit carriage 13, which contains in a known manner the devices required to operate the source 14. The support arm 15 of the source 14 is coupled in an accurately fitting and defined fashion to the holder 7 such that the focus F of the source 14, which in practice is a three-dimensional focusing zone, is situated without complicated aligning processes in the beam path of the central beam ZS of an X-ray bundle emitted by the X-ray source 10. Despite the coupling of the therapy unit 2 to the C-arm X-ray apparatus 1, specifically of the support arm 15 to the holder 7, the C-arm 9 of the C-arm X-ray apparatus 1 can be adjusted together with the X-ray system relative to the source 14 along its circumference in the bearing assembly 8 (orbital movement), and can be adjusted relative to the holder 7 along the axis B within certain limits, which can be influenced by the shape of the support arm 15, together with the bearing assembly 8 around the axis B (angulation) and together with the bearing assembly 8 in the direction of the double arrow b. The medical system provided with the therapy unit 2 and the C-arm X-ray apparatus 1 in this case has degrees of freedom such that the source 14 can be aligned relative to a patient P supported on a patient bed 17, making it possible for the patient bed 17 to be designed without any movement axes.

In the case of the present exemplary embodiment, the support arm 15 of the source 14 is arranged on the holder 7 in a defined way such that the focus F of the source 14 is situated not only in the beam path of the central beam ZS of the X-ray bundle, but also at the isocenter IZ of the C-arm 9. The isocentric adjustment of the C-arm 9 makes it possible in this case for body tissue KG of the patient P, who is indicated in FIG. 1 only schematically and is supported on the patient bed 17, once the body tissue KG has been positioned at the isocenter IZ of the C-arm 9, to always be located in the central beam ZS of the X-ray bundle when the X-ray system is being adjusted relative to the body tissue KG, without the X-ray system having to be readjusted for the purpose of taking X-ray images of the body tissue KG from different projection directions. Since the focus F of the source 14 likewise remains at the isocenter IZ, it is possible, for example, to apply focused acoustic waves to the body tissue KG, and at the same time to monitor the progress of the treatment from different projection angles by means of X-rays by independently adjusting the X-ray system relative to the source 14.

Figure 3:
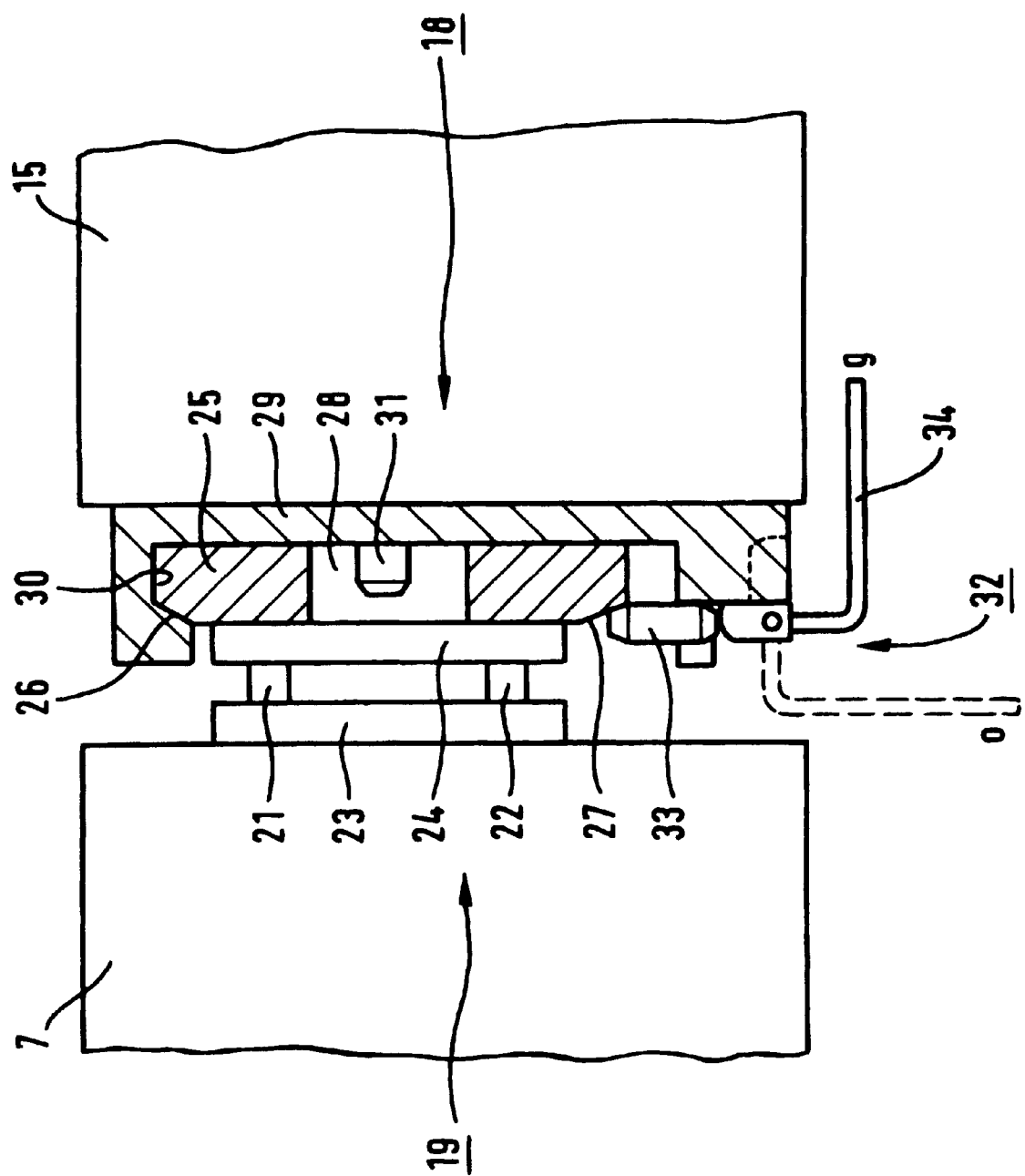
FIG. 3 shows a view, partly in section, of the coupling device of the support arm and the coupling device of the X-ray apparatus for coupling the therapy unit to the X-ray apparatus.

FIG. 3 shows an exemplary embodiment of a coupling device 18 for the support arm 15, and a coupling device 19 of the C-arm X-ray apparatus 1, which serve the purpose of coupling the therapy unit 2 to the C-arm X-ray apparatus 1 in an accurately fitted and defined fashion. In the case of the present exemplary embodiment, the coupling device 19 is fitted to the holder 7, for example by means of screws (not shown in FIG. 3), and the coupling device 18 is fitted to the support arm 15, for example likewise by means of screws (not shown in FIG. 3).

The coupling device 19 has two plates 23, 24 connected by pins, of which only pins 21, 22 are visible in FIG. 3, and a coupling plate 25 provided with positioning aids fitted to the plate 24. As positioning aids, the coupling plate 25 has positioning noses 26, 27 and an approximately vertically extending aperture 28.

The coupling device 18 of the support arm 15 has a base plate 29 which is provided with a positioning groove 30, a positioning bolt 31 and a mechanism 32 for locking the coupling device 18 of the support arm 15 to the coupling device 19 of the supporting part 7. The mechanism 32 includes a clamping bracket 34 which acts on a locking bolt 33 and whose positions of open o and closed g are illustrated in FIG. 3.

Figure 4:
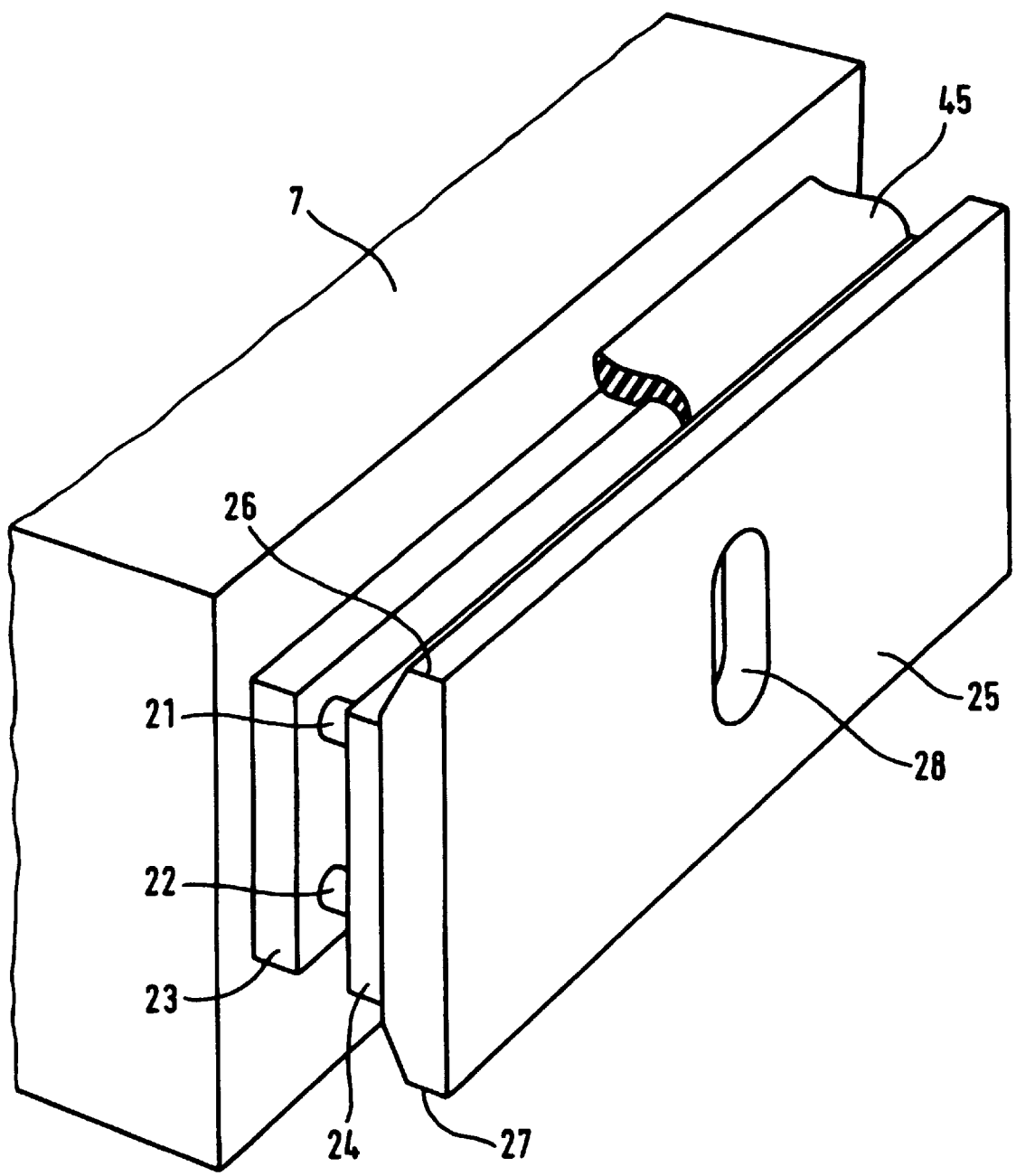
FIG. 4 shows a view of the coupling device of the X-ray apparatus from FIG. 3.

FIG. 4 shows a view of the coupling device 19 of FIG. 3, with a schematically indicated cover 34 for the coupling device 19, the vertical shape and orientation of the aperture being clearly in FIG. 4.

Thus, in the exemplary embodiment, the therapy unit 2 is coupled to the C-arm X-ray apparatus 1 by coupling the coupling device 18 of the support arm 15 to the coupling device 19 of the holder 7. In this case, the brakes are initially released. Such brakes are not shown in more detail but are known and are necessarily present, and serve to fix the vertically adjustable and rotatable lifting column 6 of the C-arm X-ray apparatus 1. Subsequently, for example, the therapy unit 2 is moved adjacent up to the C-arm X-ray apparatus 1 so that the positioning bolt 31 of the coupling device 18, which can be spring-loaded, engages in an accurately fitted fashion in the aperture 28 in the coupling plate 25 of the coupling device 19, and the base plate 29 of the coupling device 18 of the support arm 15 comes to bear at least partially against the coupling plate 25 of the coupling device 19. In order to achieve this, the holder 7 arranged on the lifting column 6 may, if necessary, be adjusted somewhat vertically, with the lifting column 6. By virtue of the fact that the brakes of the lifting column 6 are released, the holder 7 or the coupling device 19 can be aligned relative to the coupling device 18 of the support arm 15, so that the base plate 29 is brought to bear relatively flat against the coupling plate 25. Subsequently, the lifting column 6 is vertically adjusted such that the positioning nose 26 of the coupling plate 25 comes to be situated in an accurately fitted fashion in the positioning groove 30 of the coupling device 18, the positioning bolt 31 moving in the vertical direction in the aperture 28. Thereafter, the mechanism 32 is locked by closing the clamping bracket 34, the locking bolt 33 being moved out and clamped to the coupling plate 25. Following thereupon, the brakes of the lifting column 6 are applied, thus concluding the coupling of the therapy unit 2 to the C-arm X-ray apparatus 1.

Depending on the application, the support arm 15 can subsequently be removed from the holder 35 of the unit carriage 13 of the therapy unit 2, and the carriage 13 of the therapy unit 2 can be removed from the C-arm X-ray apparatus 1 (see FIG. 1), or can remain on the C-arm X-ray apparatus 1 (see FIG. 2). However, it need not necessarily be possible to remove the support arm 15 from the holder 35.

The coupling device 18 of the support arm 15, and the coupling device 19 of the C-arm X-ray apparatus 1 can differ from those described in the present exemplary embodiment. For example, the positioning groove 30 can be arranged at the bottom, and the mechanism 32 can be arranged at the top on the device 18. Furthermore, the coupling device 19 can be arranged on the support arm 15, and the coupling device 18 can be arranged on the holder 7. Also, the positioning aids of the coupling device 18 and of the coupling device 19 can differ within the scope of the invention from the embodiments described.

Figure 2:
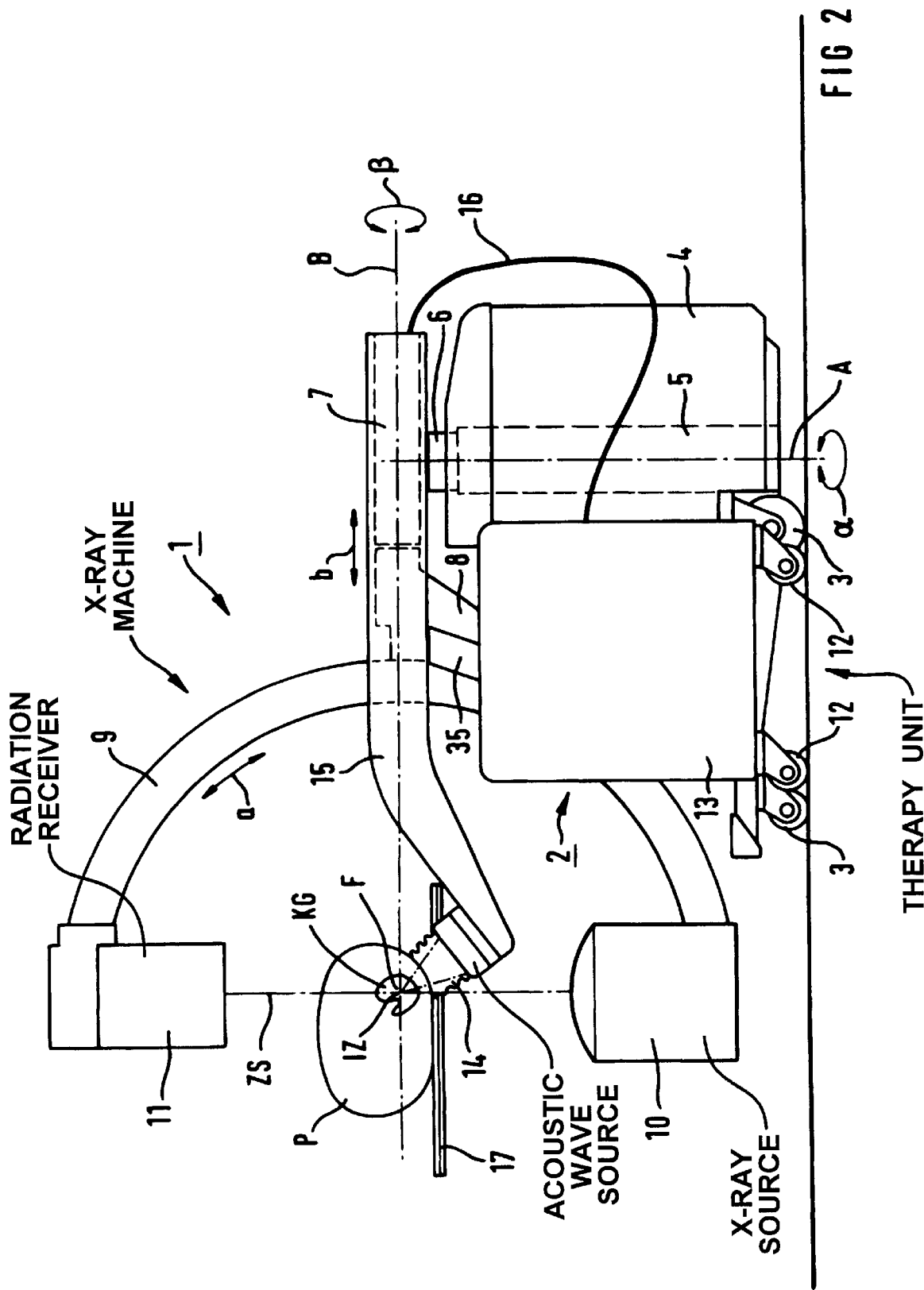
FIG. 2 shows the medical system according to the invention from FIG. 1, in which the therapy unit is arranged next to the X-ray apparatus, the support arm of the source remaining on the holder of the therapy unit.
Figure 5:
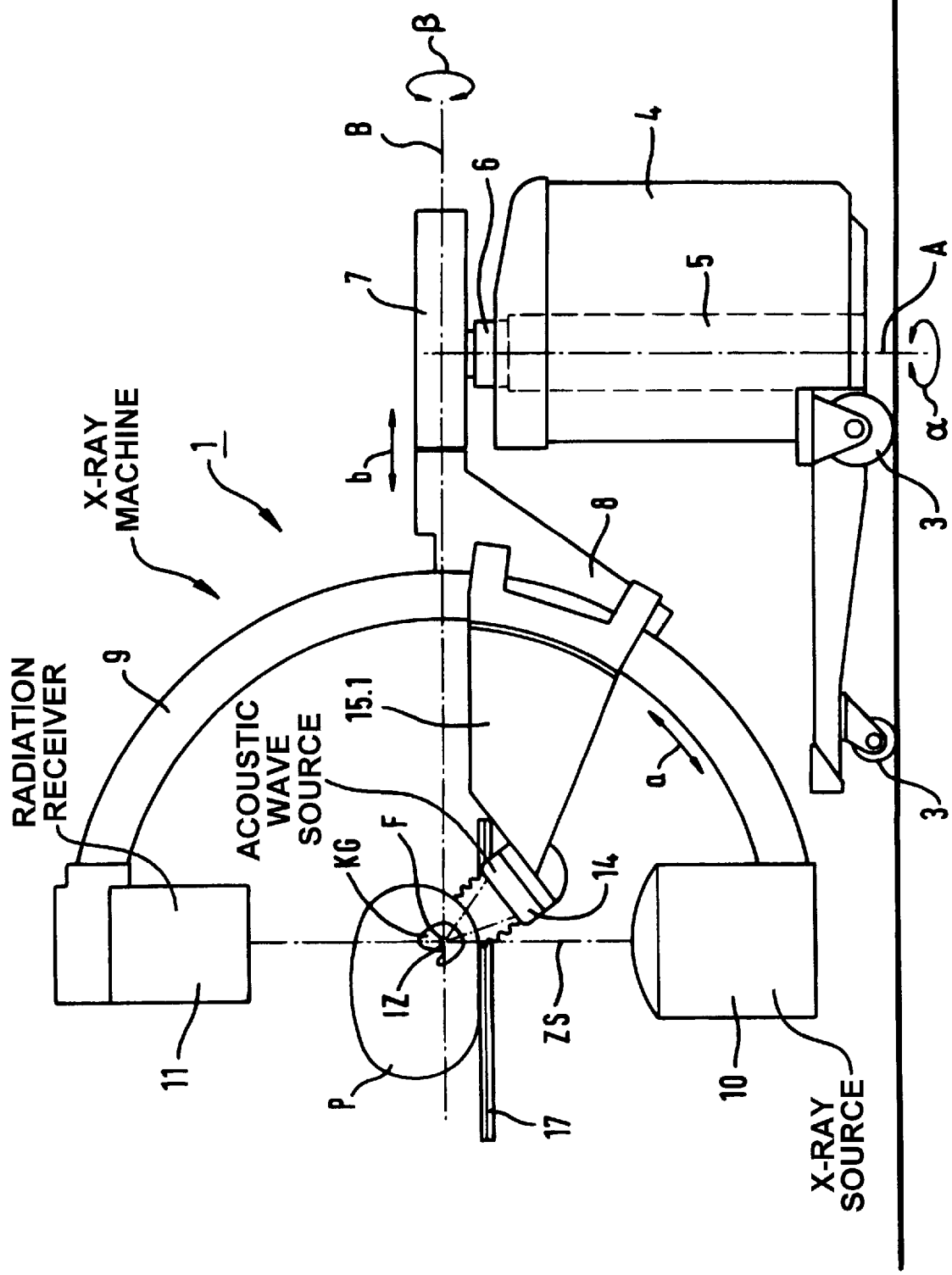
FIG. 5 shows another embodiment of the inventive medical system, wherein the support arm of the acoustic wave source is coupled to the bearing assembly of the X-ray apparatus.
Figure 6:
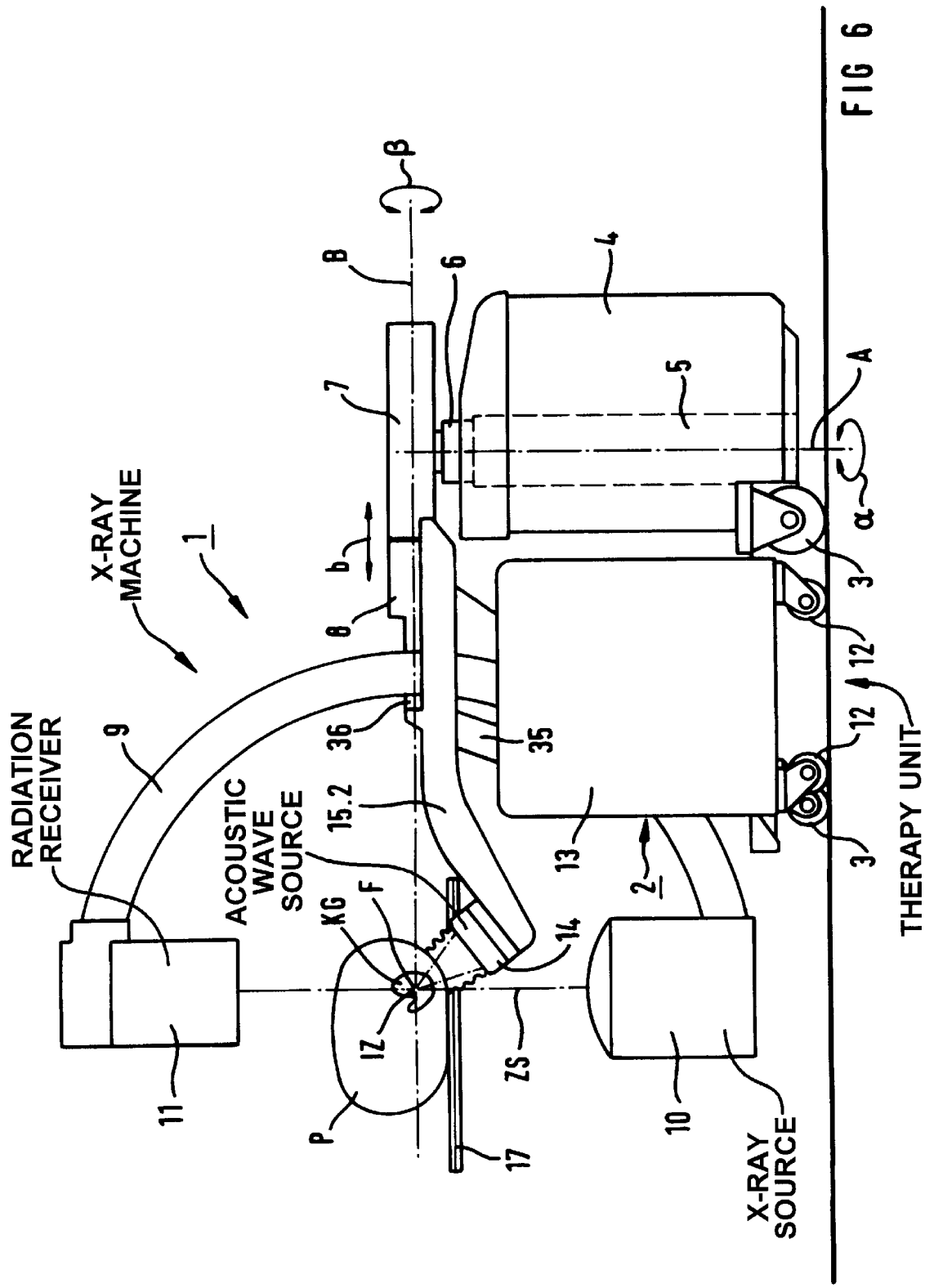
FIG. 6 shows a further embodiment of the inventive medical system, wherein the support arm of the source is coupled to the carrier of the x-ray system of the X-ray apparatus.
Figure 7:
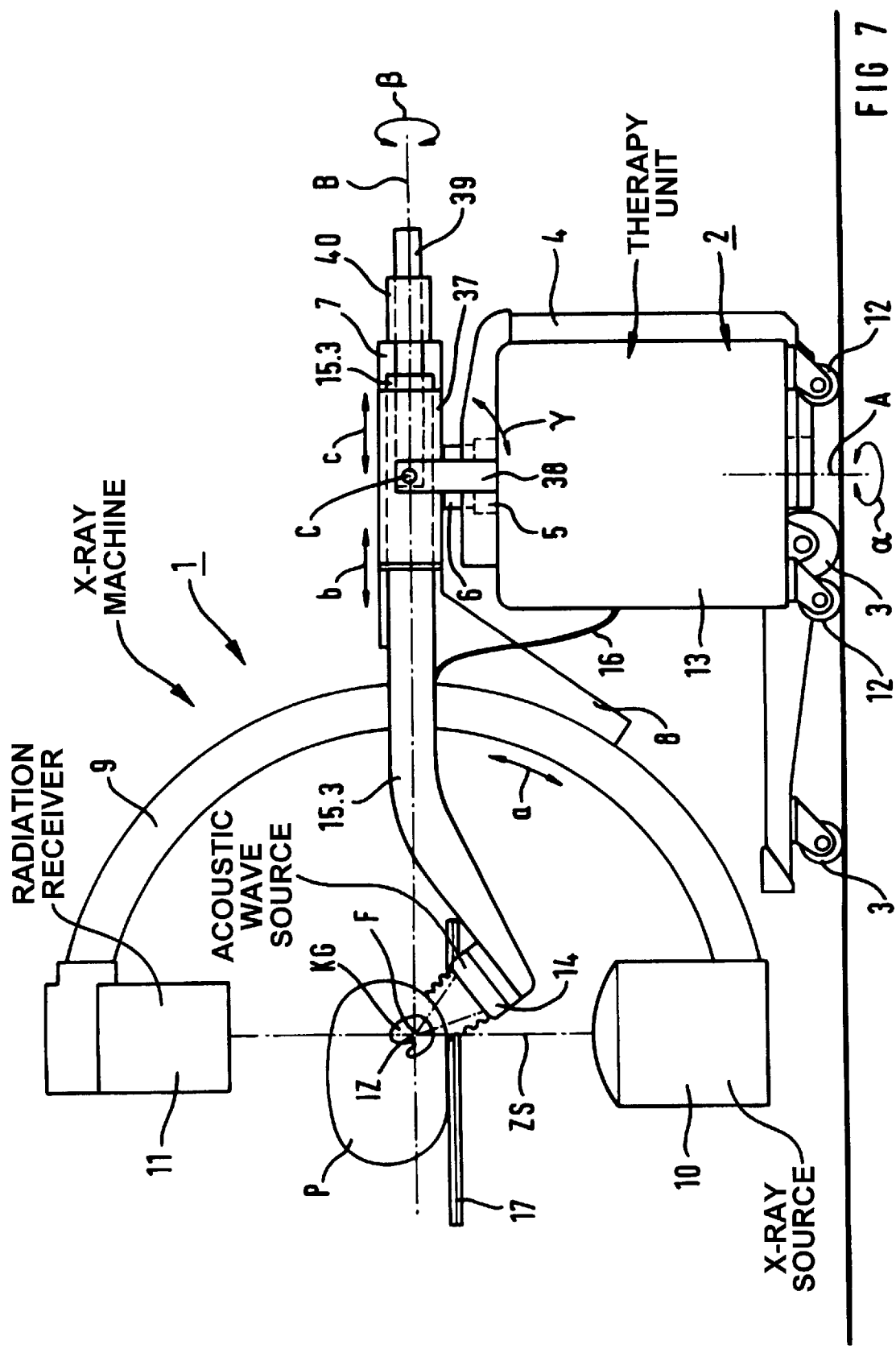
FIG. 7 shows an embodiment of the inventive medical system wherein the support arm is mounted in a bearing device which is coupled to the holder of the X-ray apparatus.

FIGS. 5, 6 and 7 show further embodiments of the medical system according to the invention, wherein components of the medical system embodiments of FIGS. 5, 6 and 7 which are approximately the same in terms of function and design as components of the medical system from FIG. 1 and FIG. 2 being provided with the same reference symbols.

FIG. 5 shows an embodiment of the medical system in which the support arm 15.1 of the therapy unit 2 is coupled to the bearing assembly 8 of the C-arm X-ray apparatus 1, the carriage of the therapy unit 2 not being shown in FIG. 5. The support arm 15.1 is designed so that the C-arm 9 can still be adjusted relative to the source 14 along its circumference in the bearing assembly 8 in the direction of the double arrow a (orbital movement). Furthermore, the C-arm 9 arranged on the bearing assembly 8 can be pivoted about the axis B of the bearing assembly 8 together with the support arm 15.1 and the source 14. In the case of FIG. 5, the support arm 15.1 is coupled to the bearing assembly 8 so that the focus F of the source 14 coincides with the isocenter IZ of the C-arm 9.

FIG. 6 shows a further embodiment of a medical system according to the invention, in which the support arm 15.2 of the therapy unit 2 is coupled to the C-arm 9. The carriage 13 of the therapy unit 2 is designed in this case with a holder 35 for the support arm 15.2 of the source 14 for the purpose of stabilizing the support arm 15.2. In the case of the medical system from FIG. 6, the support arm 15.2 is coupled to the C-arm 9 via a pivot joint 36 which connects the support arm 15.2 and the C-arm 9 to one another. The defined fashion in which the support arm 15.2 is fitted to the pivot joint 36 aligns the therapy unit 2 relative to the C-arm X-ray apparatus 1 such that the focus F of the source 14 is situated at the isocenter IZ and in the beam path of the central beam ZS of an X-ray bundle emitted by the X-ray source 10. The pivot joint 36 has the effect in this case of allowing the C-arm 9 arranged on the bearing assembly 8 to remain capable of pivoting, at least within certain limits, around the axis B together with the bearing 8, depending on the embodiment of the support arm 15.2. Thus, the X-ray system can still be adjusted relative to the source 14 within certain limits. In this embodiment of the medical system, for reasons of stability the support arm 15.2 generally is not as a rule moved from the holder 35 of the machine carriage 13.

The support arm 15.1 can be coupled to the bearing assembly 8, and the support arm 15.2 can be coupled via the pivot joint 36 to the C-arm 9 in a similar manner to the coupling of support arm 15 to the holder 7, devices corresponding to the coupling device 18 and the coupling device 19 being provided on the support arms 15.1, 15.2, and corresponding coupling devices being provided on the bearing assembly 8 and the pivot joint 36, which are not shown in more detail in FIGS. 5 and 6. During the operation of coupling the holding arm 15.1 to the bearing assembly 8 and coupling the holding arm 15.2 to the pivot joint 36, it can be useful in this case also to release the brakes of the bearing assembly 8 so that the devices and coupling device can be aligned relative to one another.

FIG. 7 shows an embodiment of a medical system according to the invention, in which the support arm 15.3 of the source 14 is displaceably mounted in the directions of the double arrow c in a bearing device 37. The bearing device 37 is arranged on a holder 38 of the carriage 13 of the therapy unit 2. The holder 38 has a substantially horizontal axis C, around which the bearing device 37 can be pivoted in the directions of the double arrow d. This can be advantageous for transporting the therapy unit 2 to different locations. Moreover, in one embodiment the bearing device 37 can be removed from the holder 38.

In the case of the present exemplary embodiment, the bearing device 37 is coupled to the holder 7 of the X-ray apparatus 1. However, it is also possible given an appropriate design along the lines of the exemplary embodiments described in FIGS. 5 and 6, for the bearing device 37 to be coupled to the bearing assembly 8 or the C-arm 9 of the X-ray apparatus 1.

According to the invention, the bearing device 37 is coupled to the holder 7 in a defined fashion such that the focus F of the source 14 arranged on the support arm 15.3 mounted in the bearing device 37 is situated at least approximately at the isocenter IZ of the C-arm 9, and thus on the axis B and in the beam path of the central beam ZS of an X-ray bundle emitted by the X-ray source 10. In this case, the C-arm 9 can still be pivoted along its circumference in the bearing assembly 8, at least within certain limits, together with the bearing assembly 8, around the axis B, depending on the embodiment of the support arm 15.3.

Because of its displaceable bearing in the bearing device 37, the support arm 15.3 can be brought into different positions with reference to the X-ray apparatus 1 even after the bearing device 37 has been coupled to the holder 7 of the X-ray machine. The support arm 15.3 preferably can adopt at least two defined positions in the bearing device 37. One position (not shown in the figures) is adopted by the support arm 15.3 preferably when the therapy unit 2 is being transported or when the therapy unit 2 is being coupled to the X-ray machine 1, this position being distinguished by the fact that the support arm 15.3 does not project far on either side of the carriage 13 of the therapy unit 2. The second defined position is the so-called therapy position, shown in FIG. 7, of the support arm 15.3, into which the support arm 15.3 can be brought after the bearing device 37 has been coupled to the holding part 7. In this therapy position, the focus F of the source 14 arranged on the support arm 15.3 is situated approximately on the horizontal axis B and on the central beam ZS of the X-ray system.

In the case of the present exemplary embodiment, the bearing device 37 also has a holding device 39 which is anchored in the bearing device 37 and on which a drive device 40 is arranged, having an electric motor (not shown in FIG. 7). The drive device 40 is arranged so that it can be displaced in the directions of the double arrow c on the holding device 39, and can be pivoted around the holding device 39. The drive device 40 can be coupled to a drive element, for example a shaft 41, which extends through the holder 7 and is connected to the bearing assembly 8 and has the axis B. In this way, the pivoting movement of the C-arm 9 mounted in the bearing assembly 8 can be performed around the axis B by means of the drive device 40 co-operating with the shaft 41. However, the pivoting need not be performed by motor but alternatively can be performed manually, as in the cases previously described.

Figure 8:
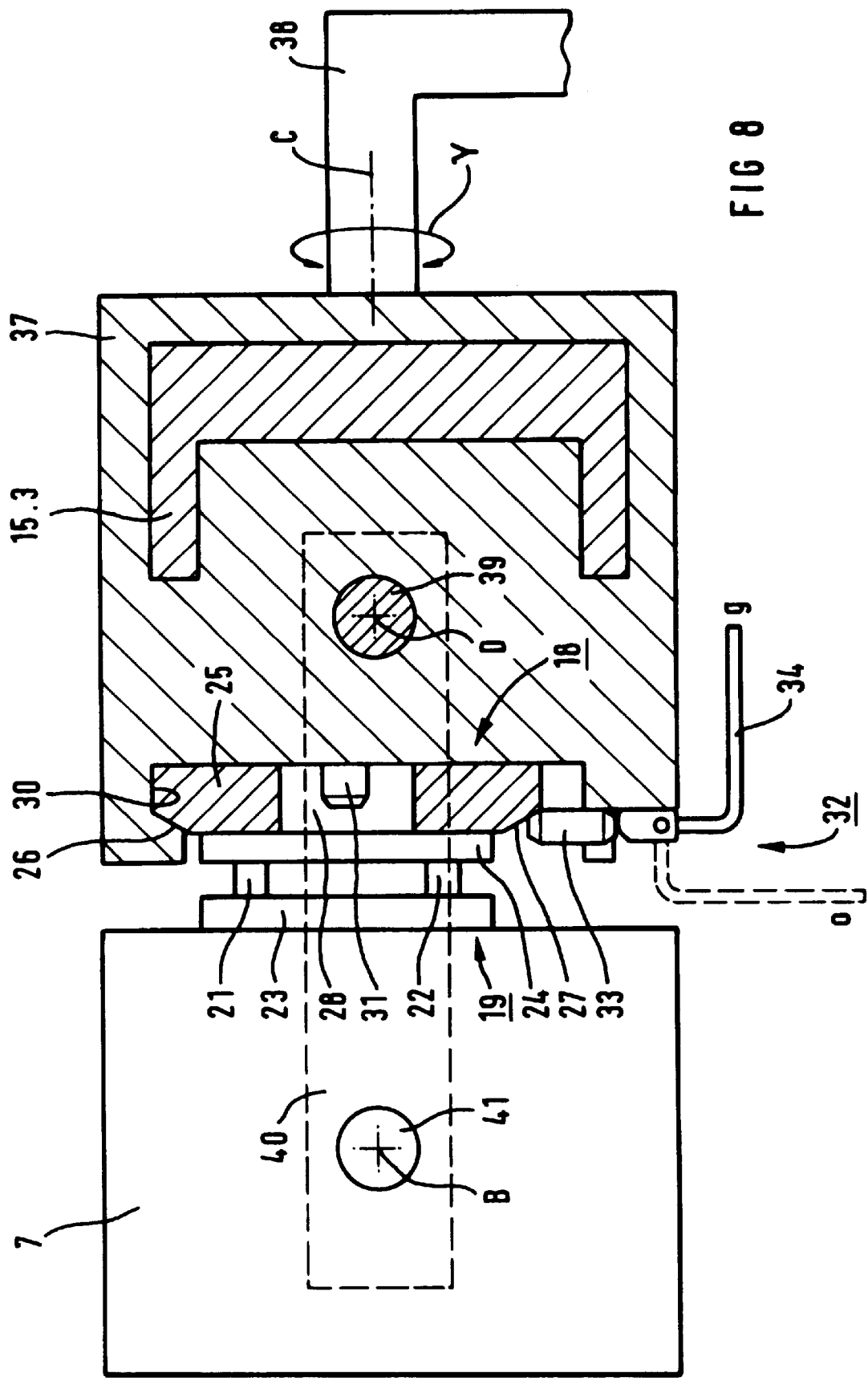
FIG. 8 shows a view partly in section, of the bearing device of the support arm with coupling device, and the coupling device of the X-ray apparatus for coupling the therapy unit to the X-ray apparatus.

FIG. 8 shows, partly in section, the coupling device of the therapy unit 2 and the coupling device of the X-ray apparatus 1, which correspond basically to the devices 18, 19 shown in FIG. 3 and are therefore provided with the same reference symbols.

By contrast with FIG. 3, the coupling device 18a in the FIG. 8 embodiment has no base plate. The bearing device 37 for the support arm 15.3 is, rather, designed so that it has the positioning groove 30, the positioning bolt 31 and the mechanism 32 for locking the coupling device 18 to the coupling device 19.

FIG. 8 shows the holder 38 with the horizontally extending axis C, the holding device 39, fixed in the bearing device 37, for the drive device 40, and the shaft 41, which extends through the holding part 7 and has the axis B. Moreover, dashed lines in FIG. 8 show the position of the drive device 40, which is coupled to the drive shaft 41 and can be pivoted about the axis D when the coupling is released.

Moreover, as is known but not shown the source 14 can have an ultrasound locating unit in addition to the X-ray locating unit.

Furthermore, the medical system can be provided, in a way not shown, with known means for image processing and with display devices on which it is possible to represent radiographs and ultrasonic images into which the position of the focus F of the source 14, the position of the isocenter IZ etc. can be mixed.

Moreover, like the source described in German OS 41 35 177, the acoustic wave source 14 of the therapy unit 2 can have a central, X-ray transparent region 14a. In this case, the support arm of the source 14 is designed, and can be coupled to the C-arm X-ray apparatus 1, such that the central beam of an X-ray bundle emitted by the X-ray source 10 essentially coincides with the acoustic axis of the source 14, and thus extends through the X-ray transparent region thereof, as shown in FIG. 9.

The medical system according to the invention has been explained above in the context of an example for treating body tissue KG of a patient P. However, the medical system can also be used in pain therapy, bone restoration or for crushing concrements in the body of a patient.

Although modifications and changes may be suggested by those skilled in the art, it is the intention of the inventor to embody within the patent warranted hereon all changes and modifications as reasonably and properly come within the scope of his contribution to the art.

We claim as our invention:

1. A medical system comprising:
   an X-ray machine having an X-ray source which emits an X-ray bundle having a central beam proceeding along a central beam path, an X-ray receiver on which said central beam is incident, and a plurality of X-ray machine components, including at least one movably adjustable X-ray machine component, which participate in supporting said X-ray source and said X-ray receiver, and adjustment means, including said at least one movably adjustable X-ray machine component, for adjusting said X-ray source and said X-ray receiver together with said at least one of said X-ray machine components relative to an examination subject in at least one adjustment direction selected from the group consisting of vertical adjustment and pivoting around a horizontal axis;
   a therapy unit including an acoustic wave source which emits acoustic waves converging at a focus, and a support arm on which said acoustic wave source is mounted; and
   means for detachably coupling said support arm to said at least one movably adjustable X-ray machine component for situating said focus of said acoustic wave source substantially on said horizontal axis and in said central beam path, and for allowing adjustment of said X-ray source and said X-ray receiver relative to said acoustic wave source.

2. A medical system as claimed in claim 1 wherein said acoustic wave source has a central X-ray transparent region through which said central beam path proceeds when said support arm is coupled to said at least one of said X-ray machine components.

3. A medical system as claimed in claim 1 wherein said plurality of X-ray machine components which participate in supporting said X-ray source and said X-ray receiver comprise a carrier on which said X-ray source and said X-ray receiver are mounted, a holder, and a bearing assembly connecting said carrier to said holder.

4. A medical system as claimed in claim 3 wherein said carrier comprises a C-arm having a circumference, and wherein said bearing assembly comprises means for adjusting said C-arm along said circumference.

5. A medical system as claimed in claim 4 wherein said carrier has an isocenter.

6. A medical system as claimed in claim 3 wherein said horizontal axis proceeds through said holder, and wherein said holder comprises means for pivoting said bearing assembly and said carrier around said horizontal axis.

7. A medical system as claimed in claim 6 wherein said therapy unit includes
   a drive device and said holder of said X-ray machine includes a drive element, said drive element extending through said holder and being connected to said bearing assembly and containing said horizontal axis, said drive device via said drive element pivoting said bearing assembly and said carrier around said horizontal axis.

8. A medical system as claimed in claim 7 wherein said therapy unit includes a holder on which a bearing device is disposed, said support arm being displaceably mounted in said bearing device, and said bearing device comprising a holding device and said drive device being arranged on said holding device.

9. A medical system as claimed in claim 8 wherein said drive device is arranged on said holding device so as to be displaceable in a displacement direction selected from the group consisting of longitudinal displacement and pivoting around said holding device.

10. A medical system as claimed in claim 9 wherein said bearing device is removably disposed on said holder.

11. A medical system as claimed in claim 8 wherein said holder has a substantially horizontal axis and comprises means for pivoting said bearing device around said horizontal axis.

12. A medical system as claimed in claim 1 wherein said therapy unit includes holder means to which said support arm with said acoustic wave source mounted thereon is removably disposed.

13. A medical system as claimed in claim 1 wherein said therapy unit comprises a holder and a bearing device disposed on said holder, said support arm being dislaceably mounted in said bearing device.

14. A medical system as claimed in claim 13 wherein said bearing device is removably disposed on said holder.

15. A medical system as claimed in claim 13 wherein said holder has a substantially horizontal axis and comprises means for pivoting said bearing device around said horizontal axis.

16. A medical system as claimed in claim 13 wherein said plurality of X-ray machine components participating in supporting said X-ray source and said X-ray receiver include a carrier to which said X-ray source and said X-ray receiver are mounted, a holder, and a bearing assembly connecting said carrier to said holder, and wherein said means for detachably coupling comprises a first coupling device attached to said carrier, and a second coupling device, engaging said first coupling device, attached to said bearing device.

17. A medical system as claimed in claim 13 wherein said plurality of X-ray machine components participating in supporting said X-ray source and said X-ray receiver include a carrier to which said X-ray source and said X-ray receiver are mounted, a holder, and a bearing assembly connecting said carrier to said holder, and wherein said means for detachably coupling comprises a first coupling device attached to said bearing assembly, and a second coupling device, engaging said first coupling device, attached to said bearing device.

18. A medical system as claimed in claim 13 wherein said plurality of X-ray machine components participating in supporting said X-ray source and said X-ray receiver include a carrier to which said X-ray source and said X-ray receiver are mounted, a holder, and a bearing assembly connecting said carrier to said holder, and wherein said means for detachably coupling comprises a first coupling device attached to said holder of said X-ray machine, and a second coupling device, engaging said first coupling device, attached to said bearing device.

19. A medical system as claimed in claim 1 wherein said plurality of X-ray machine components participating in supporting said X-ray source and said X-ray receiver include a carrier to which said X-ray source and said X-ray receiver are mounted, a holder, and a bearing assembly connecting said carrier to said holder, and wherein said means for detachably coupling comprises a first coupling device attached to said carrier, and a second coupling device, engaging said first coupling device, attached to said support arm.

20. A medical system as claimed in claim 1 wherein said plurality of X-ray machine components participating in supporting said X-ray source and said X-ray receiver include a carrier to which said X-ray source and said X-ray receiver are mounted, a holder, and a bearing assembly connecting said carrier to said holder, and wherein said means for detachably coupling comprises a first coupling device attached to said bearing assembly, and a second coupling device, engaging said first coupling device, attached to said support arm.

21. A medical system as claimed in claim 1 wherein said plurality of X-ray machine components participating in supporting said X-ray source and said X-ray receiver include a carrier to which said X-ray source and said X-ray receiver are mounted, a holder, and a support arm connecting said carrier to said holder, and wherein said means for detachably coupling comprises a first coupling device attached to said holder of said X-ray machine, and a second coupling device, engaging said first coupling device, attached to said support arm.

22. A medical system as claimed in claim 1 wherein said means for detachably coupling comprises a first coupling device attached to said one of said X-ray machine components and a second coupling device, engaging said first coupling device, attached to said therapy unit.

23. A medical system as claimed in claim 22 wherein each of said first coupling device and said second coupling device has positioning aids for assisting in aligning and engaging said first coupling device and said second coupling device.

24. A medical system as claimed in claim 23 wherein said first coupling device comprises a coupling plate carrying said positioning aids, said positioning aids comprising a nose on said coupling plate and a substantially vertically oriented aperture in said coupling plate, and wherein said positioning aids of said second coupling device comprise a positioning groove at said therapy unit and a positioning bolt at said therapy unit, said positioning bolt, during coupling of said first coupling device and said second coupling device, engaging said aperture and said nose engaging said groove.

25. A medical system as claimed in claim 22 wherein said first coupling device comprises a mechanism for locking said first coupling device to said second coupling device.

* * * * *